(12) United States Patent
Paliwal et al.

(10) Patent No.: US 9,656,262 B2
(45) Date of Patent: May 23, 2017

(54) MICROFLUIDIC GRID-BASED DESIGN FOR HIGH THROUGHPUT ASSAYS

(71) Applicants: Saurabh Paliwal, Mountain View, CA (US); Zhizhong Yin, Timonium, MD (US); Raymond Cheong, Timonium, MD (US)

(72) Inventors: Saurabh Paliwal, Mountain View, CA (US); Zhizhong Yin, Timonium, MD (US); Raymond Cheong, Timonium, MD (US)

(73) Assignee: EUVEDA BIOSCIENCES, INC., Timonium, MD (US)

( * ) Notice: Subject to any disclaimer, the term of this patent is extended or adjusted under 35 U.S.C. 154(b) by 283 days.

(21) Appl. No.: 14/301,319

(22) Filed: Jun. 10, 2014

(65) Prior Publication Data

US 2015/0355165 A1     Dec. 10, 2015

(51) Int. Cl.
*B01L 3/00*     (2006.01)
*C12N 5/00*     (2006.01)

(52) U.S. Cl.
CPC ... *B01L 3/502761* (2013.01); *B01L 3/502738* (2013.01); *C12N 5/0018* (2013.01); *B01L 2300/0829* (2013.01); *B01L 2300/0864* (2013.01); *B01L 2300/0874* (2013.01); *B01L 2300/0883* (2013.01); *B01L 2400/0487* (2013.01); *B01L 2400/0655* (2013.01)

(58) Field of Classification Search
CPC ............ B01L 3/5027; B01L 3/502746; B01L 3/502715; B01L 3/502738; B01L 2300/0816

USPC .......................................... 422/502, 503, 99
See application file for complete search history.

(56) References Cited

U.S. PATENT DOCUMENTS

| | | | | |
|---|---|---|---|---|
| 6,696,022 B1* | 2/2004 | Chan | ...................... | B01F 5/061 422/500 |
| 7,611,673 B2* | 11/2009 | Kartalov | ............ | B01L 3/50273 422/502 |
| 8,496,889 B2* | 7/2013 | Rajagopal | ......... | B01L 3/502753 209/132 |
| 8,936,762 B2* | 1/2015 | Ehrlich | .................. | G01N 15/14 422/400 |
| 2004/0208792 A1* | 10/2004 | Linton | .................. | B01L 3/5025 422/552 |

(Continued)

*Primary Examiner* — Nina Bhat

(57) ABSTRACT

Microfluidic devices have been developed to perform a range of high-throughput biochemical and cell-based assays over recent years. A design for a microfluidic device has been developed that resembles a microtiter plate, by placing the test chambers (each test chamber contains cells) and top-loading drug inlets (at least one per test chamber) in a grid according to the ANSI/SBS standards, yet offers the miniaturization and fluid handling advantages of microfluidics. This ensures that the device design is compatible with fluid handling and imaging equipment already in use for drug screening. A range of topologies have been determined that allow placement of various elements of this microfluidic network within the grid alignment constraints. A resistance equalization methodology has also been developed to reduce variability across assays run in different chambers of the microfluidic device. Additionally, it offers orders of magnitude miniaturization over multiwell plates, and potentially more reliable fluid handling.

20 Claims, 15 Drawing Sheets

(56) References Cited

U.S. PATENT DOCUMENTS

| | | | | |
|---|---|---|---|---|
| 2007/0026381 A1* | 2/2007 | Huang | ............. | B01L 3/502746 435/4 |
| 2007/0243523 A1* | 10/2007 | Ionescu-Zanetti | | B01L 3/502738 435/4 |
| 2008/0248960 A1* | 10/2008 | Hong | ................ | B01L 3/502738 506/7 |
| 2011/0027804 A1* | 2/2011 | Yarmush | ............ | G01N 33/5044 435/7.21 |

* cited by examiner

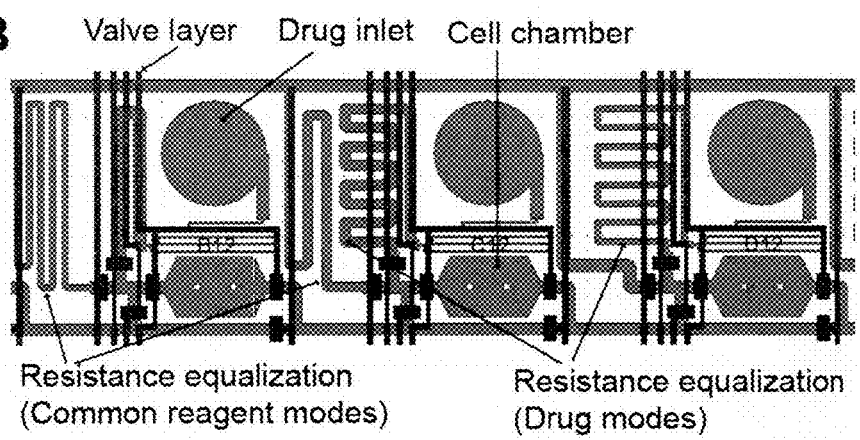
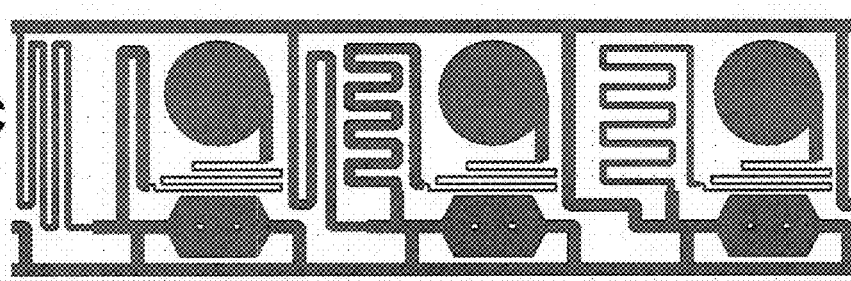
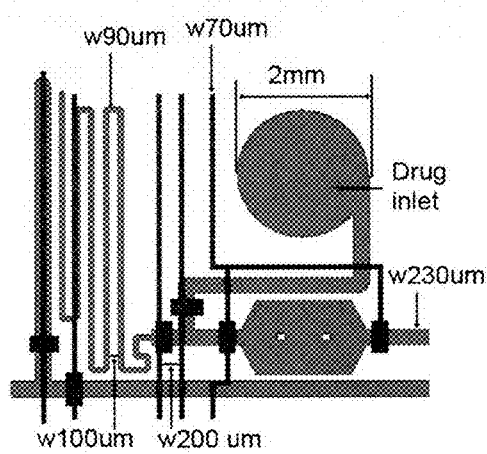

MICROFLUIDIC GRID-BASED DESIGN FOR HIGH THROUGHPUT ASSAYS

STATEMENT REGARDING FEDERALLY SPONSORED RESEARCH OR DEVELOPMENT

This research was funded in part by a Small Business Innovation Research (SBIR) grant I P—1142913 from the National Science Foundation (NSF)

CROSS-REFERENCE TO RELATED APPLICATIONS

This application claims the benefit of U.S. Provisional Application No. 61/833,459 filed Jun. 11, 2013. The entire contents of the aforementioned application are hereby incorporated herein by reference.

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC HUNG SYSTEM (EFS-WEB)

Not Applicable

STATEMENT REGARDING PRIOR DISCLOSURES BY THE INVENTOR OR A JOINT INVENTOR

Not Applicable

BACKGROUND OF THE INVENTION

1) Field of the Invention

The present invention relates to the general fields of microfluidics, cell based assays, and/or high-throughput assays.

2) Description of Related Art Including Information Disclosed Under 37 CFR 1.97 and 1.98

Biochemical and cell-based assays are widely used for basic biological and clinical research, as well as commercial applications such as drug screening, diagnostics etc. Typically, biochemical assays and cell-based assays are performed in multi-well plates, but this approach has several drawbacks. Multi-well plates at the throughput levels of 6-well, 24-well, 48-well, 96-well and 394-well require large numbers of cells per well and high volumes of expensive biochemicals. This prevents the performance of cell-based assays using precious cell types such as primary cells e.g. from patient biopsies, stems cells etc., and also increases the cost of cell-based assays. On the other end, multiwell plates at the 1536-well and 3456-well throughput require expensive liquid handling machines to operate them, and suffer from issues such as fluid evaporation, that create challenges to use them for cell-based assays.

Microfluidics involves fluid flow inside chips fabricated with features at the micrometer scale, and thus offers the ability to manipulate fluid flow at very small volumes. However, there is a lack of microfluidic grid-based devices that allow for the performance of high-throughput biochemical and cell-based assays in a miniaturized manner, are compatible with existing fluid handling and imaging technologies that are typically used for multiwell plates, that allow multiple modes of fluidic operation, and have essentially similar flow rates through different reaction units within the device.

BRIEF SUMMARY OF THE INVENTION

We have demonstrated the feasibility of a novel microfluidic chip for use in highly miniaturized high-throughput cell-based and biochemical assays. We developed a specific device design (for simplicity, we will refer to this design with the codename "ArrayChip" in this document, and was previously referred to as "Shenandoah" in the Provisional Application No. 61/833,459) that would have test chambers just 40 nL in size (compared to ~5 uL for a 1536-well plate and ~200 ul for a 96-well plate). We tested the design's flow properties (Section A), determined the operating conditions needed to support living cells (Section B), and demonstrated its use in a pilot experiment (Section C).

In order to test the underlying design, we fabricated devices having 32 cell chambers and ran experiments using water and dye to visualize fluid flow within the device. Through such experiments, we discovered significant flow non-uniformity in the originally proposed design. This flaw caused flow rates to be different through different cell chambers, which would interfere with controlled comparisons between the chambers. Through mathematical analysis, numerical simulation, and additional empirical flow measurements, we determined the microchannel network resistance needed to achieve equal flow rates. New devices were fabricated based upon this network and were shown to have a high degree of flow uniformity. Another problem we encountered was long delays in the response time of integrated valves, which we eliminated by decreasing the length of the microchannels that control the valves. These design modifications led to a smooth scale up to a functional ArrayChip device having 96 chambers. Similar modifications can be used to increase the throughput to 384 chambers, 1536 chambers etc.

To determine the operating conditions needed to support living cells, we focused on flow rates compatible with cell viability, as shear stress due to fluid flow is the major impediment to using cells within microfluidic devices. In simplified 8-chamber devices, we conducted water/dye experiments to determine, at various flow rates, the minimum time needed to ensure complete fluid turnover in the cell chambers. We then exposed cells within the cell chambers to the same flow conditions, finding that cells tend to ball up in response to flow but then spread back out. ACHN, a renal carcinoma cell line, displayed only a mild balling response and was used for subsequent experiments. Then, we determined the operating conditions needed to reproduce identical flow conditions within the full scale 96-chamber device.

Finally, we demonstrated that the 96-chamber ArrayChip device could be used in cell-based assays. We determined a full protocol to introduce cells, drug solutions, and visualization reagents into the device. Then, we ran a pilot experiment in which we exposed ACHN cells to various doses of an agonist and used immunofluorescence (with signaling-specific antibodies) to readout the response. This experiment was performed using typical equipment available to drug screening researchers, such as automated imaging platforms. We also identified potential improvements (e.g. increasing cell chamber height) that could further improve the operation and reliability of the technology.

BRIEF DESCRIPTION OF THE DRAWINGS

FIG. 8B: Zoom-in view of the design in FIG. 8A, displaying the fluidic layer (light gray) and control or valve layer (dark gray). Functional units B12 to D12 are displayed, each consisting of the cell chambers, drug inlets, channels with appropriate resistance equalization for common reagent modes (e.g. flushing the same reagent through all cell chambers, or till the edge of the cell chamber) and drug addition modes, as well as valves to control the fluid flow through different channels.

FIG. 8C: Zoom-in view of the fluidic layer of functional units B12 to D12

FIG. 8D: Some typical dimensions of the device, wherein "w90 um" refers to a width of 90 um.

DEFINITIONS

Figure 1:
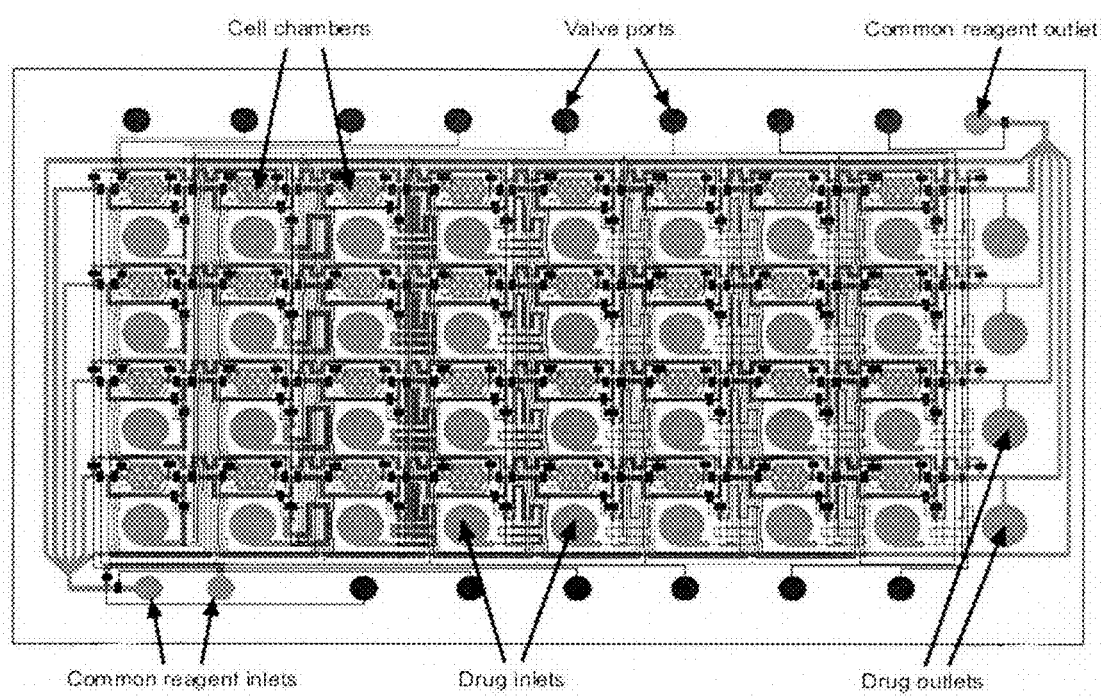
FIG. 1: Example design of a 32-chamber microfluidic chip. The fluidic layer is shown in light gray and the valve layer (control layer) is in dark gray. The elements are arranged on a 4.5 mm grid (same as a 384-well plate). (Some channels connecting to the drug inlets appear to have a dark gray color due to the grayscale rendering and overlying control layer channels, but they are in fact fluidic layer channels).

The instant invention is most clearly understood with reference to the following definitions.

A "fluid layer" is any layer of a device in which fluid channels are incorporated. In the context of the instant invention, the fluid layer is typically the bottom layer of the device.

A "fluid channel" is a channel through which fluid and/or air can flow wherein the channel is part of the fluid layer. Fluid channels are functionally connected to both inlet and outlet ports optionally by connection through other fluid channels. Fluid channels are preferably rounded to improve sealing of the fluid channels by valves.

"Test chambers" are chambers that are operably connected to the different channels and inlets of each independent reaction region (unit) in the device. It is directly connected on both sides by the central channel. The test chamber is where the main reaction steps typically take place. In the case of cell based assays, this is where the seeding of cells, attachment of cells to the substrate, exposure of cells to the biochemicals e.g. drugs, fixation and staining of cells, and observation of cell behavior microscopically, is performed. Resistance of the channels connecting the top channel, the bottom channel, the central channel or the external inlet (drug inlet) to the test chamber are modified to ensure equal fluid flow rates through the test chambers. Such resistance and flow rate modeling parameters can be readily determined by one of ordinary skill in the art using mathematical or empirical modeling. The size of a test chambers is dependent on the type and number of cells on which the reaction is to be performed. Test chambers are also interchangeably referred to as cell chambers during the rest of this text. In a preferred embodiment of the invention, the test chambers are placed in a regular grid, wherein the pitch size (distance in the horizontal row direction or vertical column direction) is the same, and is the same as the pitch size of a corresponding multiwell plate based on ANSI/SBS standards.

A "central channel" is a channel composed of a series of smaller central channels which flank (lie on both sides) of the test chambers and connect the test chambers in a row to each other. Fluid flow exclusively through the central channel should therefore also pass through the test chambers.

A "top channel" is a channel that lies above the test chamber, and is operably connected to the test chamber through a channel whose resistance can be varied to get essentially equal flow rate through the different test chambers. The top channel is also referred interchangeably as a top bypass channel or top flow-through channel in this text.

By actuation of the correct valves, fluid flow can take place in a top channel without entering the test chamber. In a preferred embodiment of the invention, it is used to deliver media and chemical reagents throughout the chip, without their entering the test chamber. At an appropriate time, the appropriate valves are opened to deliver the contents of the top channel to the test chamber at the same time.

A "bottom channel" is a channel that lies below the test chamber, and is operably connected to the test chamber through a channel whose resistance can be varied to get essentially equal flow rate in the test chambers. The bottom channel is also referred interchangeably as a bottom bypass channel or bottom flow-through channel in this text. By actuation of the correct valves, fluid flow can take place in a bottom channel without entering the test chamber. In a preferred embodiment of the invention, it is used to remove media and chemical reagents from the test chamber following actuation of the appropriate valves.

A "external inlet" is a inlet corresponding to a specific test chamber, which is operably connected to the test chamber through a channel whose resistance can be varied to ensure essentially equal fluid flow rate through the different test chambers. In a preferred embodiment, it can be used to receive chemicals, biochemicals, cells, media etc. from the external world through pipette tips or similar delivery mechanisms. It is also referred interchangeably as a drug inlet in this text. In a preferred embodiment of the invention, the external inlets are placed in a regular grid, wherein the pitch size (distance in the horizontal row direction or vertical column direction) is the same, and is the same as the pitch size of a corresponding multiwell plate based on ANSI/SBS standards.

A "reaction unit" is a unit by which the microfluidic devices of the invention are organized. A reaction unit includes at least one test chamber (cell chamber), at least one external inlet (drug inlet), a central channel connecting the different test chambers, a top channel or a bottom channel or both, and the channels (with variable resistance) operably connecting the different elements of the reaction unit to the test chamber such that flow rates through the different test chambers are essentially the same. In a preferred embodiment of the invention, the reaction units are placed in a regular grid, wherein the pitch size (distance in the horizontal row direction or vertical column direction) is the same, and is the same as the pitch size of a corresponding multi-well plate based on ANSI/SBS standards.

A "control layer" is the layer in which controllers, control channels, and valves are incorporated. In a preferred embodiment of the invention, the control layer is the top layer of the device. The control layer could also be placed below the fluidic layer.

A "supercontrol layer" is a layer which also contains controllers, control channels and valve lines. In a preferred embodiment of the invention, it lies next to the control layer such that the control layer separates and lies in between the supercontrol layer and the fluidic layer.

A "valve" is a component of the device that regulates flow through a fluid channel of the device by substantially inhibiting flow through the fluid channel upon closure. Substantially inhibiting the flow means that flow is inhibited at least 80%, preferably at least 90%, more preferably at least 95%, even more preferably at least 99%, most preferably flow is completely (i.e., 100%) inhibited. In a preferred embodiment, a valve is a portion of a dead end channel (i.e., open on one end only at a control layer inlet). The valve is located adjacent to, typically above, a channel in the fluid layer and is sufficiently wide to inhibit and preferably close off flow through the adjacent fluid channel. The size of the valve is dependent on the size and shape of the fluid channel and the amount of pressure required to close the valve. In a preferred method, the channel and control valve cross perpendicularly. Upon actuation of the valve, preferably by hydrostatic pressure, the channel closes and opens.

A "valve controller" is the opening in the control layer at the end of a control channel, distal from the valve(s), that can be operably linked to a device (e.g., a syringe) to modulate the pressure in the control channel.

A "control channel" operably links a valve controller to its valve(s). A control channel is sufficiently narrow so that closure of the linked valve(s) through the valve controller does not substantially interfere with fluid flow in the fluid channels adjacent to the control channel. The critical ratio of the width of the control channel to the fluid channel may also depend on the height of the fluid channel and the thickness of the bottom layer; however, the ratio of the control to fluid channel is preferably about less than 0.25 to not substantially interfere with flow. Substantially interfere is understood as not decreasing fluid flow by more than 50%, preferably not decreasing fluid flow by more than 40%, more preferably not decreasing fluid flow by more than 30%, even more preferably not decreasing fluid flow by more than 20%, most preferably not decreasing fluid flow by more than 10%.

An "elastomeric compound" or "elastomer" is a rubber. Preferred elastomers of the instant invention are biocompatible, gas permeable, optically clear elastomers useful in soft lithography including silicone rubbers, most preferably PDMS. Other possible elastomers for use in the devices of the invention include, but are not limited to, polyisoprene, polybutadiene, polychloroprene, polyisobutylene, poly(styrene-butadiene-styrene), the polyurethanes, and silicone polymers; or poly(bis(fluoroalkoxy)phosphazene) (PNF, Eypel-F), poly(carborane-siloxanes) (Dexsil), poly(acrylonitrile-butadiene)(nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), and polytertrafluoroethylene (Teflon).

A "compound to modulate cell adhesion" includes natural compounds, such as an extracellular matrix (ECM) component is a protein (e.g., fibronectin, laminin, integrin, collagen), peptide (e.g., RGD binding site), carbohydrate, or other chemical compound (e.g., extracellular signaling molecule) present in the ECM that controls cell attachment and/or migration. Non-ECM components (e.g., poly-lysine, gelatin, antibodies) are also known to modulate cell adhesion. Compounds to modulate cell adhesion in the instant invention preferably promote cell adhesion.

An "active agent" is a compound that modulates the activity of a cell or can be visualized using microscopy. Active agents include, but are not limited to, a naturally or non-naturally occurring molecules including agonists, antagonists, nutrient sources, signal transduction molecules, peptides, carbohydrates, nucleic acids, drugs or therapeutic agents, dyes, and fluorescent tags.

"Essentially equal flow" is understood such that the variation of the rate of flow in the different test chambers in the device is preferably less than 50% of the mean flow rate through the test chambers, more preferably less than 20% of the mean flow rate, more preferably less than 10% of the mean flow rate, more preferably less than 5% of the mean flow rate, and most preferably less than 1% of the mean flow rate.

"Essentially equal time of introduction of fluid" is understood such that the time of introduction of fluid into a test chamber shows variation that is preferably less than 50% of the mean time of introduction of a new fluid in the test chambers following the actuation of a specific set of valves, more preferably less than 20% of the mean time of introduction, more preferably less than 10% of the mean time of introduction, more preferably less than 5% of the mean time of introduction, and most preferably less than 1% of the mean time of introduction. The essentially equal flow rate is understood to lead to an essentially equal time of introduction of a new chemical or media in the test chambers all across the device.

DETAILED DESCRIPTION OF THE INVENTION

The result of this invention is a range of microfluidic chip design that would be appropriate for use in high-throughput drug screening applications, by designing it to be compatible with existing robotic liquid handlers and imaging equipment. To achieve this goal, we designed a microfluidic chip design in which the top-loading drug inlets and cell chambers are arranged in a grid spacing according to the ANSI/SBS standards for the locations of microtiter wells. In such a design, drugs can be transferred into the chip using standard fluid dispensers, and cell responses can be imaged with standard robotic microscopes. We performed three tasks to demonstrate the functionality of the design:

Section A: Scale up the device design to accommodate 96- and 384-drugs in parallel
Section B: Determine operating conditions and procedures that support cell experimentation
Section C: Perform a pilot experiment to screen drugs on cells in the device In the remainder of this document, we detail the research effort undertaken to fulfill the three tasks and the overall objective.

Section A: Scale Up the Device Design to Accommodate 96- and 384-Drugs in Parallel The basic design concept employed for this chip was to ensure that the drug inlets and cell chambers are each arranged in a grid spacing defined by ANSI/SBS standards for the locations of multiwell plates. Consequently, the chip is organized as a grid of functional units, wherein each functional unit consists of a cell chamber and a corresponding drug inlet. Within each unit, the cell chamber and drug inlet are connected by a channel whose flow can be regulated by an integrated valve. Additionally, channels and integrated valves connect each unit to master inlets and outlets in a manner that prevents cross-talk between the units.

In order to retain the desired grid spacing of the cell chambers and drug inlets, the main constraint is that each functional unit and necessary channels should be contained within the well size of the multiwell plate. For instance, to ensure compatibility with standard 96-well plates, each functional unit needs to be contained within a 9×9 mm square (ANSI standards specify that the spacing between the centers of two wells in a 96-well multititer plate is 9 mm). Alternatively, for compatibility with 384-well plates, each functional unit must be contained within a 4.5×4.5 mm square. Furthermore, the cell chamber and drug inlet must be placed in a fixed position within each functional unit, to ensure that the cell chambers and drug inlets as a whole, each form grids with appropriate pitch size. An additional general design constraint is the channels controlling the integrated valves (e.g., as shown in blue in FIG. 1) cannot lie above the region of the drug inlets (since they are open to the atmosphere which would interfere with valve toggling) and also should not lie above the cell chambers in order to avoid imaging artifacts.

In order to provide a common proof-of-concept of this ArrayChip design for both a 96-chamber and 384-chamber design, we decided to develop a microfluidic chip with 96-chambers at a miniaturization level corresponding to a 384-well plate, i.e. wherein each of the 96 functional units is contained inside a 4.5×4.5 mm square. Since, the miniaturization is more stringent at a 384-scale, the ArrayChip design would display that our 96-chamber chip can be readily expanded to the 384-chamber throughput, albeit with the need for potential recalculation of resistances due to increased channel lengths. For the same reason, the ArrayChip design would allow us to show that a 96-chamber chip at 96-scale (where each functional unit is contained inside a 9×9 mm square) would be easy to achieve, since the tolerances are less stringent at the larger scale. Again, the expansion of the size of each functional unit and the overall chip would require some resistance recalculations, due to the increased path length of certain channels, as illustrated through the example described below. We present below some of the important design improvements that we made to generate the proof-of-concept for the ArrayChip design.

A.1 ArrayChip v.1.0

We first fabricated and tested a 32-chamber device (FIG. 1), in which the chambers are in a grid with spacing corresponding to that of a 384-well plate (4.5 mm pitch). We will refer to this design henceforth as ArrayChip v.1.0.

In ArrayChip v.1.0, the cell chamber is sized to be at least 40 nL in volume, so that it can accommodate at least 300 cells at typical cell seeding densities (of ~$9\times10^6$ cells/mL), and consequently occupies ~25% of the functional unit. The drug inlet is sized to be ~2 mm in diameter, similar to the orifice of a well in a 1536-well plate, and also occupies about 25% of the functional unit. This leaves limited space for the channels and valves required to allow parallel operation of each functional unit, especially to ensure simultaneous and uniform addition of reagents into the cell chamber, whether that reagent is provided through the drug inlets or master inlets.

Figure 2:
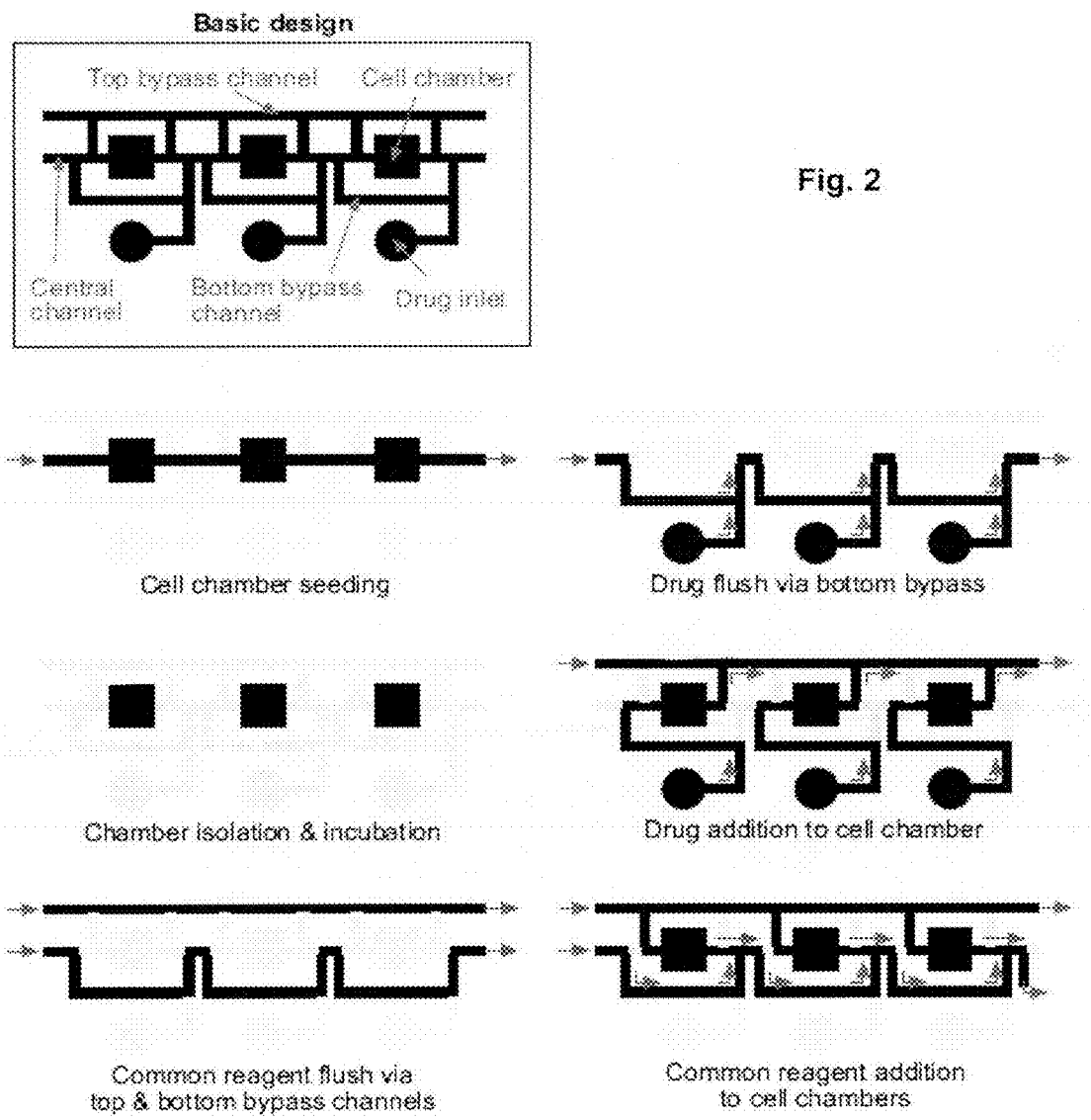
FIG. 2: Core design of the microfluidic primary cell-based assay. Top left, basic design of a single row of the device. Below, flow patterns that can be implemented in the device. In each flow pattern, channels in which valves prevent flow are shaded in gray, and channels with active flow are shaded in black.

To accommodate the necessary microfluidic elements, we evaluated the compact design shown in FIG. 2. The schematic depicts three functional units from a single row in the device, which can then be further duplicated as needed. In the design, there is a central channel passing through each of the cell chambers which allows for direct cell seeding. Additionally there are top and bottom bypass channels which allow for dead volume flushing, delivery, and outflow of common reagents (i.e. fluids to be simultaneously introduced to all cell chambers). These same channels similarly allow for flow of drug containing fluids from the drug inlets to their respective cell chambers. Appropriately placed valves allow the flow pattern to be dynamically reconfigured, thus allowing this single channel network to handle all of the different fluid handling steps of a cell-based assay.

Using soft lithography methods, we fabricated the ArrayChip v.1.0 device then tested it to see if the flow rates through the cell chambers were uniform, a crucial requirement for high throughput assays (e.g., so that fluid handling from chamber to chamber is the same and results will be comparable). We first filled the device with plain water and then introduced food coloring dye (to aid with visualization) through one of the master inlets. Using the flush modes (FIG. 2), we displaced water in the dead volume with dye, thus bringing the dye up to the entrance of the cell chambers.

Figure 3:
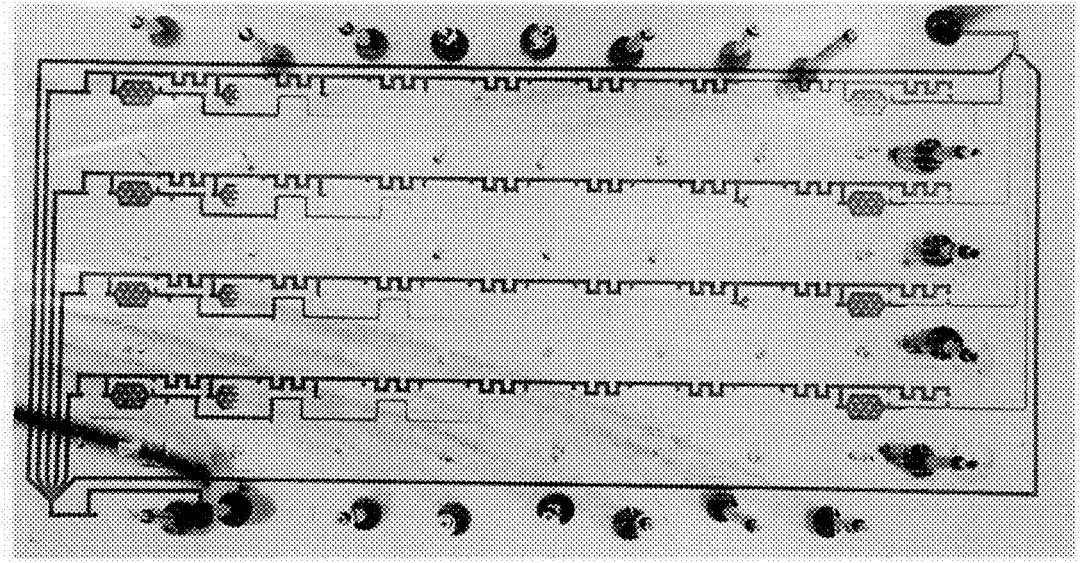
FIG. 3: Non-uniform flow of dye into the cell chambers of the ArrayChip v.1.0 device. This snapshot shows that the outer columns of chambers fill with dye faster than the inner columns.

Then, we switched to the common reagent addition mode (FIG. 2) and allowed dye to flow simultaneously into all of the cell chambers, using the dye wavefront to indicate the flow rate through each chamber. If the flow rate were uniform, we would observe the dye wavefront to advance through each chamber at the same speed. Instead, we observed that flow rates in the outer units of each row were much higher than flow rates in the inner units (FIG. 3). In fact, the outermost chambers were completely filled with dye before the innermost chambers received any appreciable amount of dye. Accordingly, we re-evaluated the design to understand the reason for the non-uniform flow rates, as describe below.

A.2 Resistance Calculations for Flow Rate Uniformity

Microfluidic channels have laminar flow patterns, allowing for a well-controlled characterization and simulation of flow rates through these channels. The flow rate through a microfluidic channel is determined by the pressure drop across the ends of the channel divided by the resistance of the channel to fluid flow. This is analogous to the current (flow rate of charges) passing through an electrical wire, which is obtained as a ratio of the voltage potential drop across the wire divided by the resistance of the wire.

Figure 4:
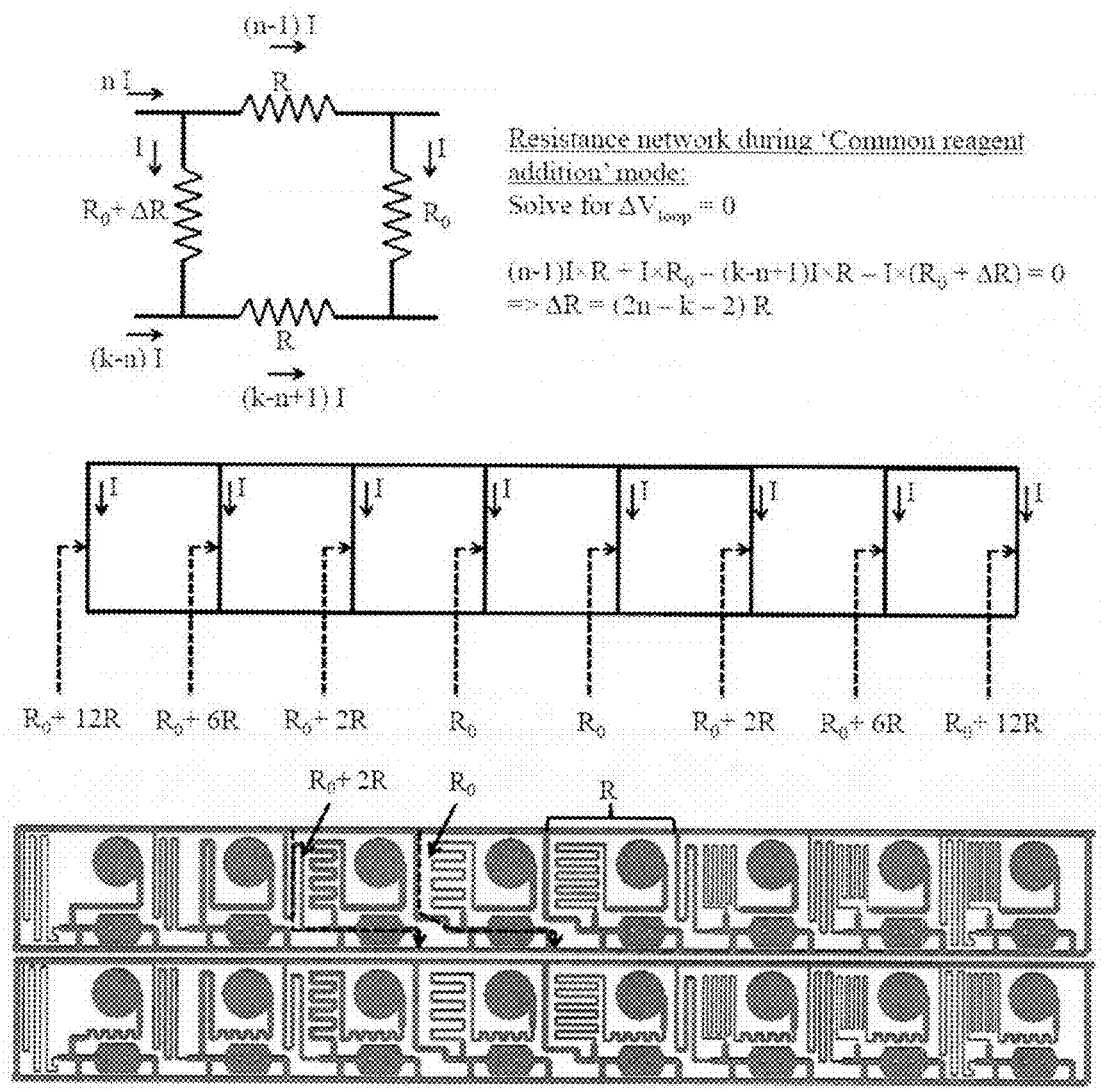
FIG. 4: Microchannel resistances needed to achieve uniform flow rate in the cell chambers. (k is the total number of chambers; n indexes the chambers from 1 through k; I is flow rate; R, R0, and ΔR are resistances). Bottom panel displays the correspondence between the Resistance network and the actual fluidic network

With this theory in mind, we modeled the fluidic network of a functional unit as a set of electrical resistances (as shown in FIG. 4), and thus were able to model the fluid flow through a row of such functional units by calculating the current flowing through each resistance. The aim of this model was to analytically determine the resistance combinations that would lead to equal current through the cell chambers. For flow during common reagent addition mode, this analysis showed that extra resistance needed to be placed in series with the cell chambers, with the amount of extra resistance depending on the position of the functional unit along the row. A similar analysis showed that, for flow during drug addition mode, extra resistance needed to be placed in series with the drug inlet, again with the amount of resistance depending on the position of the unit. The extra resistances must be present regardless of the specific chip design, provided it has the same underlying topology.

In order to generate the required resistances, we could modify the width, height, and length of the channel, with resistance generally being proportional to length, but having a higher order relationship to width and height. For instance, one can analytically derive the resistance of cylindrical microchannels to be inversely proportional to the channel radius to the fourth power. Because our microchannels are approximately semicircular (to enable integrated valve control), and there is no known analytical solution for the resistance of such a channel geometry, we had to determine the resistance through a combination of empirical measurement and numerical simulation. Empirical measurements were obtained by fabricating test devices with microchannels of various known widths, heights, and lengths, then passing fluid (water) through the test devices at known hydrostatic pressure differences (determined by heights of the inlet and outlet fluid reservoirs) for known amounts of time. From such measurements, the resistance could be computed, with examples shown in Table 1 below.

TABLE 1

Microchannel resistance to water flow at room temperature
(Resistances given per unit length, $Pa/(m^3/s)/m$)

| Height (um) | Width (um) | Length (mm) | Empirical resistance | Simulated resistance |
|---|---|---|---|---|
| 28.9 | 240 | 23.2 | $0.4 \times 10^{15}$ | $0.5 \times 10^{15}$ |
| 26.7 | 110 | 22.8 | $1.2 \times 10^{16}$ | $1.3 \times 10^{16}$ |
| 24.8 | 72 | 22.7 | $3.2 \times 10^{16}$ | $3.6 \times 10^{16}$ |

Figure 5:
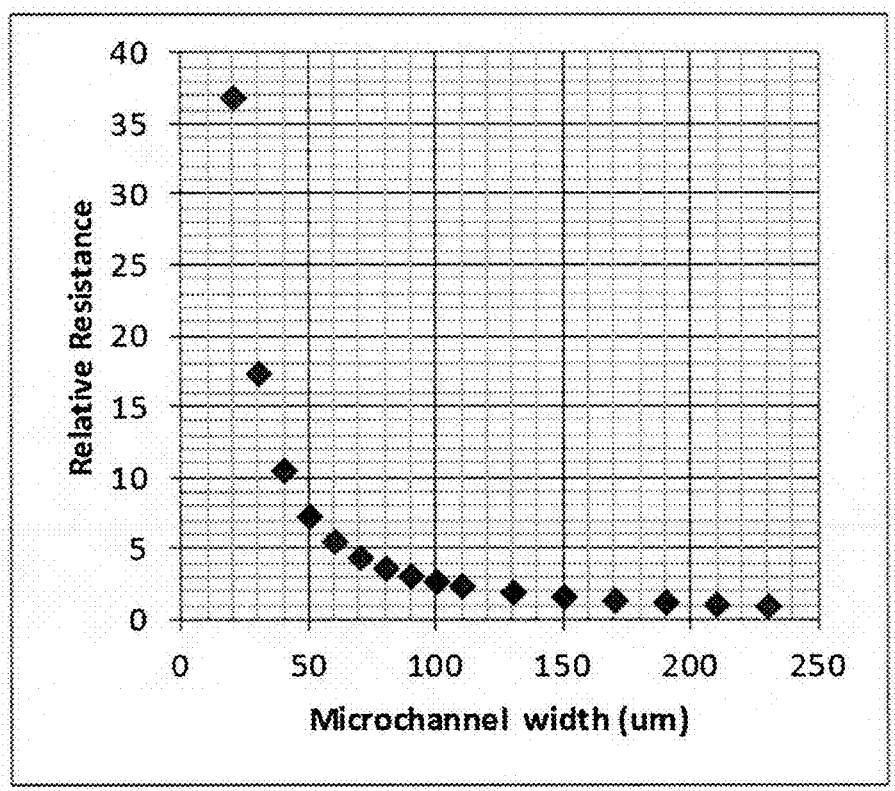
FIG. 5: Numerical simulation of microchannel resistance as a function of channel width. The channel is assumed to have semi-circular cross-section and height of ~29 um.

Using FEMLAB, we performed numerical simulations of the steady-state resistance to flow of equal sized semicircular channels. The simulated resistance values compared well with the empirical measurements (Table 1), giving us confidence that we could then use additional simulations to estimate the resistance of microchannels of other dimensions. In particular, because it is cumbersome to fabricate microchannels of different heights within the same mold, we focused on changes in resistance primarily due to microchannel width and length. The simulations showed that we could easily generate 10-fold increases in resistance by reducing the channel width from ~230 to ~40 um (FIG. 5), which was feasible to create using our soft lithography methods. Further proportional increases in resistance could be obtained, as needed, by increasing channel length. Other specific geometries could be used as well, provided they achieve the necessary calculated resistance.

A.3 ArrayChip v.2.0

Figure 6:
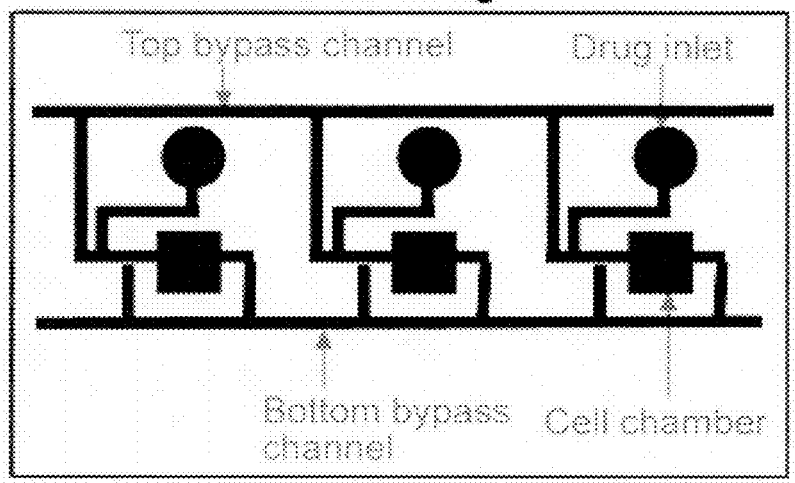
FIG. 6: ArrayChip v.2.0 design and flow uniformity. Top, basic design of the functional units in v.2.0 (compared to FIG. 2). Bottom, snapshot showing all chambers fill with dye at the same time (here, chambers are approximately ⅔ filed). Compare to the non-uniform flow shown in FIG. 3.
Figure 6:
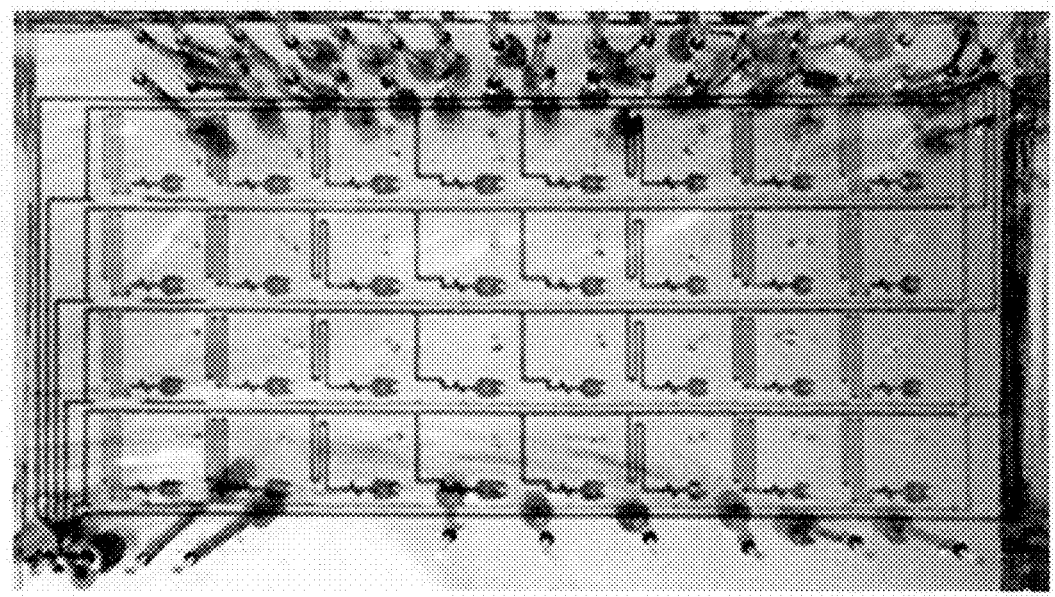

We next set out to adjust the ArrayChip design to incorporate the channel resistances needed to ensure uniform flow rates, as described above (Sec. A.2). In order to maximize the space available for high resistance serpentine channels, we swapped the locations of the cell chambers and drug inlets (which preserves their grid layout) and also reconfigured the central, bottom, and top bypass channels (FIG. 6, top). The new arrangement greatly increases the distance between the top and bottom bypass channels, and which thereby enlarges the amount of empty space within each functional unit. We then placed channels of desired resistance into this space, using serpentine channels whenever possible to modulate resistance through channel length.

The reconfigured layout has an important additional advantage in that it reduces the number of valves needed per functional unit from 7 to 5. Fewer valves simplifies the chip fabrication and should increase device reliability as well.

We then repeated the food dye flow testing in order to determine whether flow rates were indeed uniform through the chambers. As described above (Sec. A.1), if the flow rates were uniform, in this test the dye wavefront will advance through each chamber with the same speed. Indeed, we found this to be the case (FIG. 6, bottom), demonstrating that the modified channel resistances provide for uniform flow rate, thereby fixing the flaw we discovered in ArrayChip v.1.0. Likewise, we observed that the flow rate of fluid from the drug inlets to the cell chambers was uniform across the device.

Figure 7:
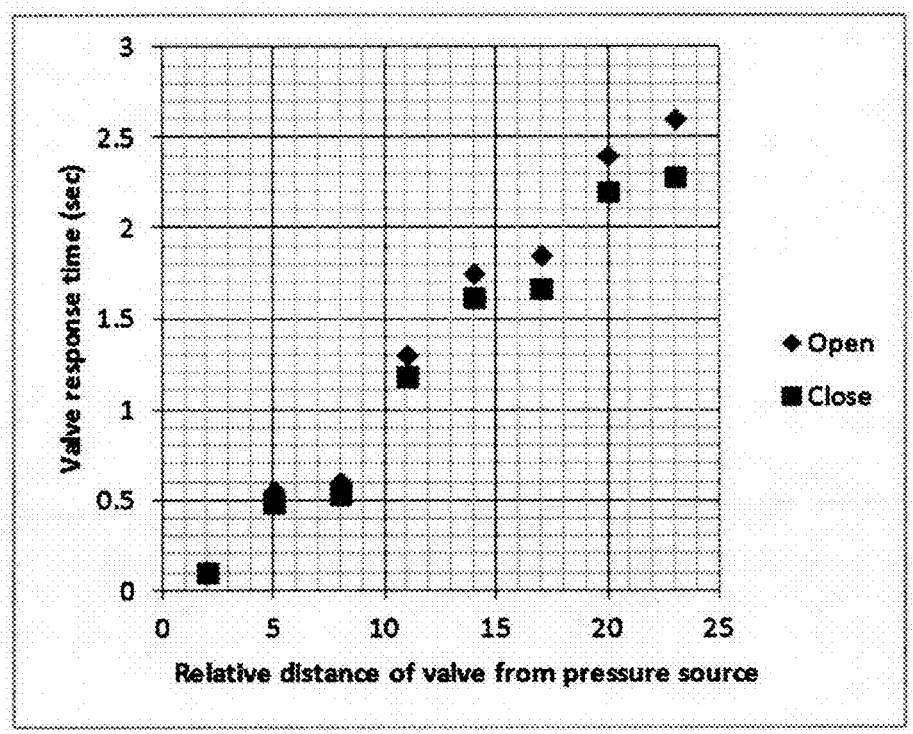
FIG. 7: Valve response delay. The plot shows time delay between toggling of pressure and complete valve opening or closing.

However, we noticed another issue in ArrayChip v.2.0 that, in retrospect, was also present in v.1.0 but masked by the flow non-uniformity. The issue was that upon applying or removing pressure, certain valves within the device closed or opened very slowly, and sometimes took 2-3 seconds to respond (FIG. 7). Noting that valves are connected by a water-filled microchannel to the pressure source that toggles them, we observed that a delay in valve opening and closing was proportional to the length of the microchannel (i.e., the distance between the valve and the pressure source). This issue could interfere with device scale-up, in which valves would be even further away from their pressure source, and hence the response delay could get more severe.

Based on further observation, we believe that the delay occurs for the following reason. Valve closure requires a volumetric expansion of the valve, so that it may compress and close the fluid channel underneath. Fluid must travel through the microchannel to fill the space created by the valve expansion. As the microchannel becomes longer, its resistance increases and it takes a longer time for the fluid to reach the valve. The same effect occurs with valve opening, although the valve shrinks and fluid flows in the opposite direction. This explanation suggests that the solution to eliminate the delay is to reduce the valve microchannel resistance by decreasing its length and/or increasing its width and height. This is the major change that we incorporated into subsequent versions of ArrayChip.

A.4 ArrayChip v.2.4

In the next version of ArrayChip, we set out to eliminate the valve response delay. In earlier versions, all valves of the same type were connected by a single long serpentine channel with the intention that those valves would all be toggled simultaneously. In version 2.1, only valves of the same type within the same column of functional units are connected together via a short straight channel. The corresponding channels from each column are then connected to a common pressure source externally. As a result, we observed that all valves now toggled simultaneously and nearly instantaneously. Furthermore, the modified valve channels did not alter the uniformity of flow rates through the cell chambers. We made other additional incremental changes (e.g., repositioning the master inlets and outlets) of a minor nature from v.2.1 to v.2.4 which do not require detailed description here. Version 2.4 is the final version that we used for subsequent characterization and research.

Figure 8A:
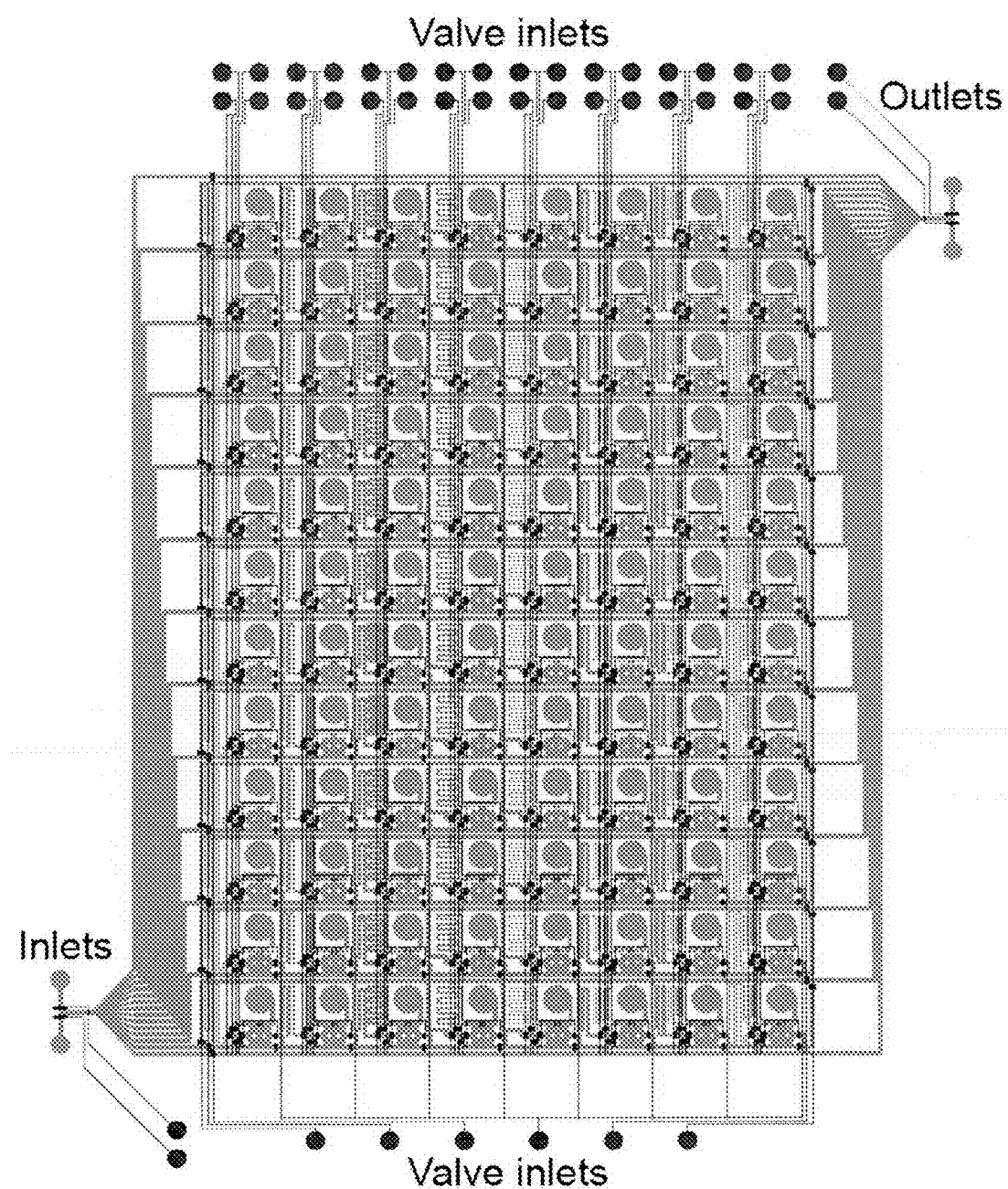
FIG. 8A: Design overview of the 96 chamber ArrayChip design (colors same as FIG. 1, where light gray corresponds to the fluidic layer and dark gray corresponds to the control/valve layer)
Figure 8E:
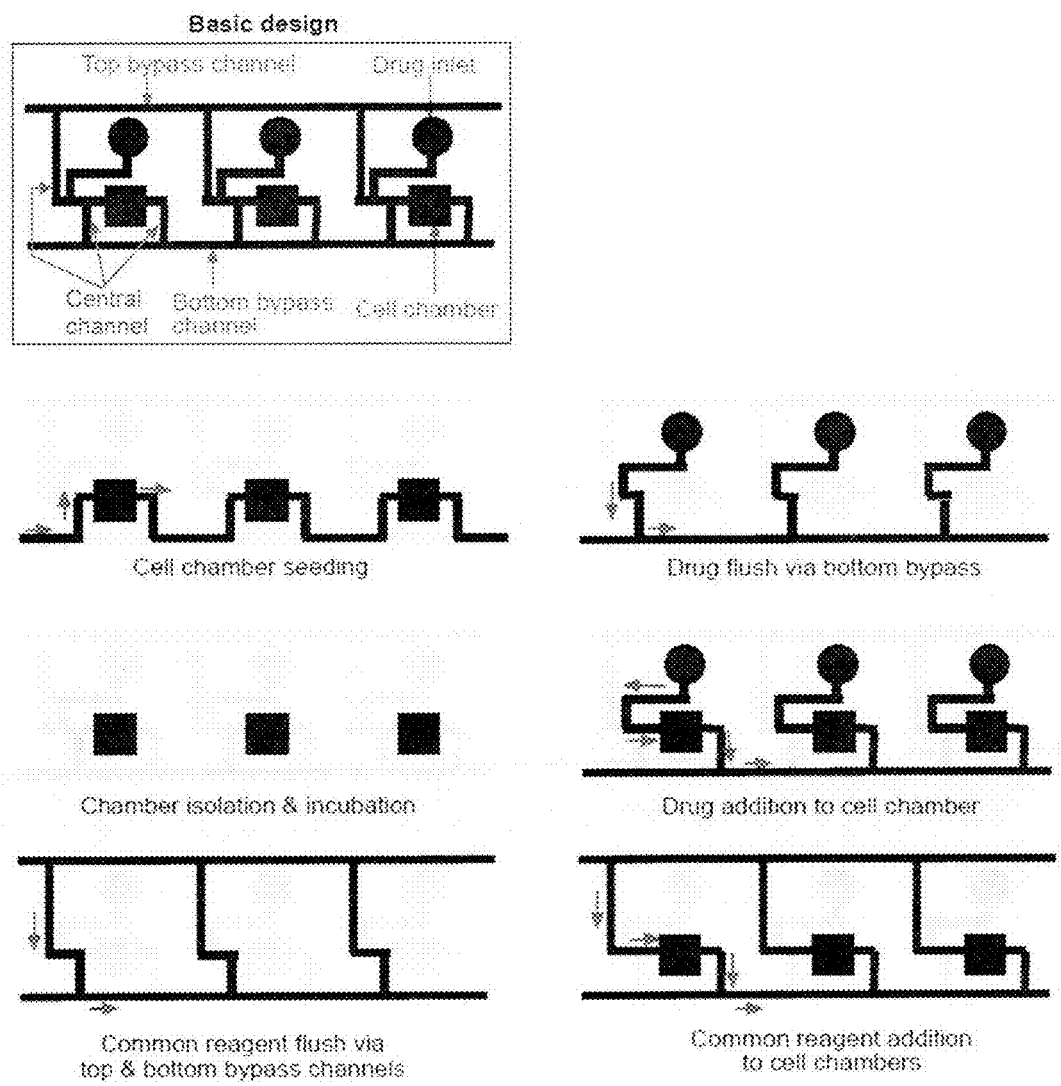
FIG. 8E: Schematic of some of the typical modes of operation of the microfluidic chip. Top, basic design of a single row of the chip. Below, flow patterns that can be implemented in the chip. In each flow pattern, channels in which valves prevent flow are shaded in gray, and channels with active flow are shaded in black.
Figure 8F:
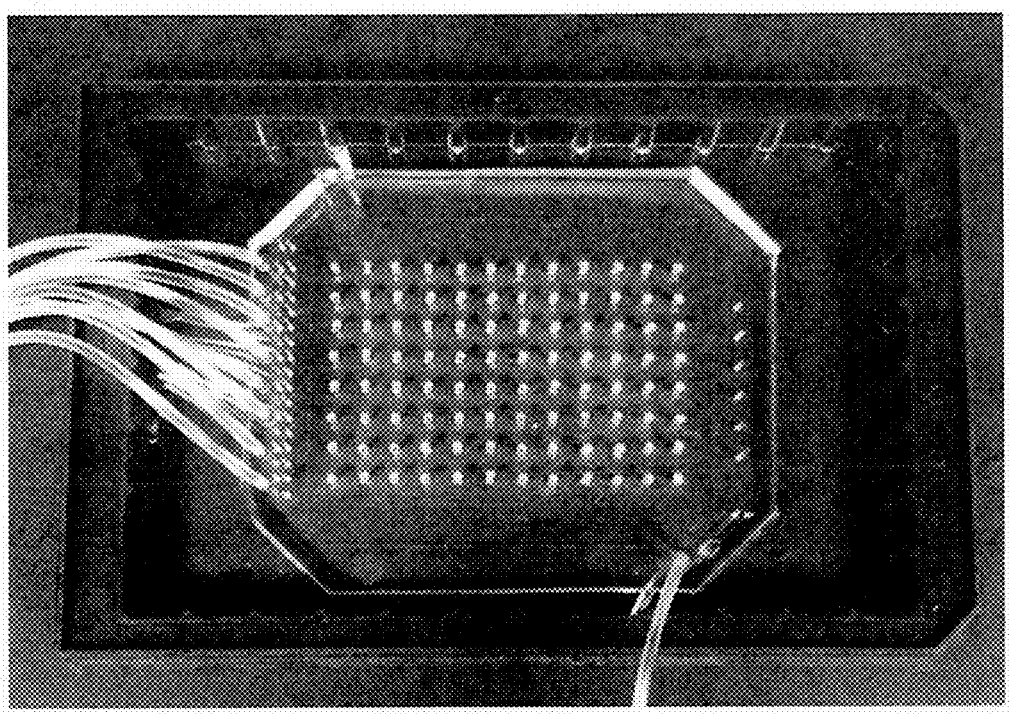
FIG. 8F: Microfluidic chip assembled in a multi-well frame.

We next created the 96-chamber edition shown in FIGS. 8A-8F: FIG. 8A shows the design overview of the whole chip, FIG. 8B and FIG. 8C show magnified views of FIG. 8A and highlights the cell chambers, drug inlets, channels and resistance equalization in the channels, FIG. 8D displays the typical dimensions of channel widths or separations FIG. 8E displays a schematic of the typical modes of operation of the chip (there can be several other combinations of valve actuation and fluid flow pressurization, leading to other modes of operation), and FIG. 8F displays an actual chip attached to a multi-well plate frame.

This required substantial re-optimization of our soft lithography protocols in order to fabricate the device in-house. In particular we encountered and solved the following technical difficulties:

Increased wafer size: In order to accommodate the larger 96-chamber device, we shifted mold fabrication from 3" to 4" silicon wafers. The larger wafers required higher photoresist spincoating speeds and/or longer spincoating times to achieve the same feature heights. Additionally, because the larger wafers had greater mass, they took longer to heat up to specific temperatures, and various bake times had to increase. Each such adjustment required trial and error to achieve identical process outputs.

Magnification factor: It is generally known that, in two-layer PDMS device fabrication, the thicker layer will shrink relative to the thin layer prior to layer-layer alignment and device assembly. Consequently, the mold for the thicker layer is slightly magnified by some percentage (typically ~1.0-1.5%). For larger devices, the precise value of the magnification factor becomes important; e.g., a 0.1% error across 10 mm results in a 10 um error which is well within alignment tolerance but the same 0.1% error across 100 mm results in a 100 um error which is well outside tolerance. We created test devices to measure the amount of shrinkage resulting from our fabrication protocols, and determined the magnification factor to within 0.05%.

Dust mitigation: The 96-chamber edition contains an area of approximately 4.5×5.5 cm in size that is 100% covered in microchannels. Any dust or flaw that affects this area would be fatal to the device. We made adjustments to increase the stringency of our fabrication (e.g. taking extra steps to remove or protect from dust) in order to achieve usable process yields.

Figure 9:
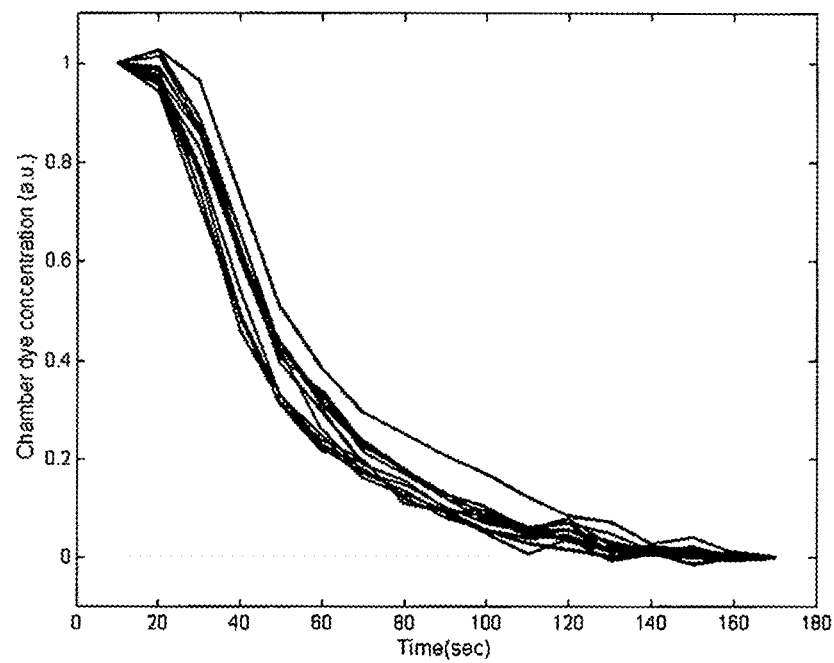
FIG. 9: Uniform fluid flow into the cell chambers of ArrayChip v.2.4. Plots show displacement of dye with water, leading to a drop in dye concentration. Representative traces from 12 cell chambers of the device are shown. Fluid exchange was complete by ~150 sec in this experiment.

As a result, we were able to fabricate flawless, reusable molds for the 96-chamber device, which we used to cast multiple chips. We then bonded the chip to a glass coverslip attached to the frame of a multi-well plate, with the drug inlets and cell chambers at their appropriate positions. Together, this represents a complete prototype of the ArrayChip chip. Additional water/dye testing confirmed that the scaled-up chip had uniform flow properties (FIG. 9).

A.5 Conclusions

We set out to create the ArrayChip chip, a microfluidic device for cell-based assays in which cell chambers and drug inlets are placed in a grid corresponding to standard multi-well plates. One of the core innovations of the design is a minimal microchannel network that implements all of the typical steps of a cell-based assay, e.g. replacement of cell media with drug solution, and replacement of drug solution with imaging reagents.

We encountered two major problems with our originally proposed design for the ArrayChip device: (1) flow rate uniformity through the cell chambers and (2) valve response delay. We fixed the flow rate uniformity problem by determining the correct pattern of microchannel resistances and incorporated them into the design, and we fixed the valve response delay by shortening the length of the valve channels. The design (v.2.4) scaled up to 96-chambers without any impingement on function, and successfully completed Section A. Because this design has dimensions corresponding to a 384-well plate (i.e. grid spacing of 4.5 mm), we expect that the design would easily scale to 384-chambers as well.

Section B: Determine Operating Conditions and Procedures that Support Cell Experimentation B.1 Shear Tolerance of Cells We set out to determine the maximum flow rate, and hence maximum shear stress, tolerated by cells cultured within the cell chambers of ArrayChip v.2.4. The maximum flow rate would provide for the minimum amount of time to completely exchange fluids within the cell chamber (e.g., exchange plain cell media with media containing a dissolved drug). To expedite this effort, we created 8-chamber editions of v.2.4, corresponding to a single row of functional units. Because of their smaller overall size, we were able to more easily fabricate such devices in bulk and then test various flow rates in parallel.

Using these devices we first determined how to precisely generate different desired flow rates by performing a water/dye experiment to measure the relationship between flow rate and inlet-outlet pressure difference. We found that the two were directly proportional, as expected, with pressure differences between 7.5-30 in $H_2O$ (0.34-1.4 psi) able to drive flow rates sufficient to fully exchange fluid within the cell chambers in 120-30 seconds, respectively. Such fluid exchange times would be more than sufficient for cell-based assay drug screening especially in comparison to typical drug incubation times of hours or days.

Figure 10:
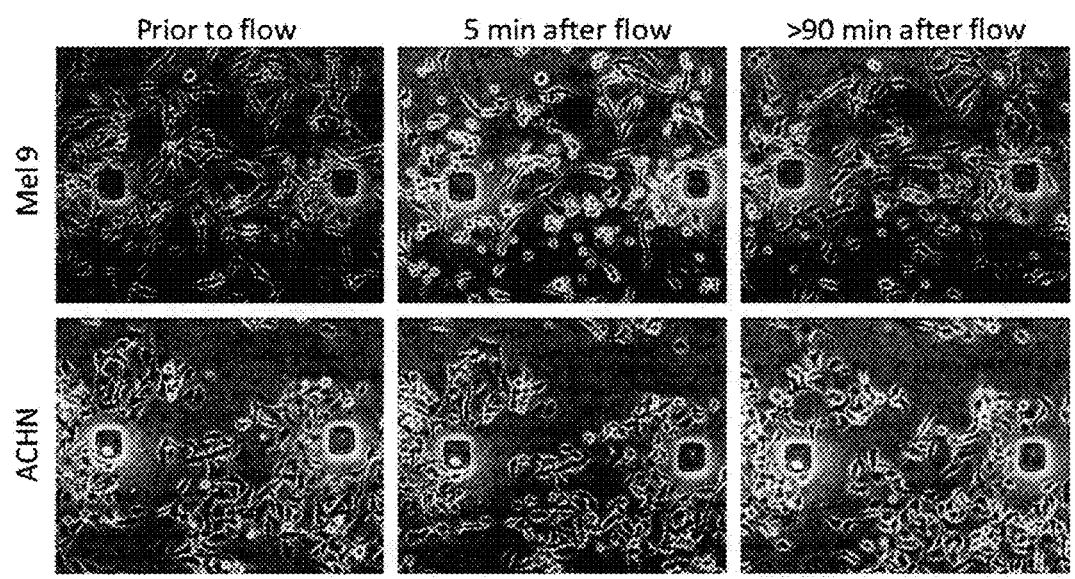
FIG. 10: Response of cells to shear stress during complete fluid turnover of the cell chambers. Mel9 and ACHN cells balled up quickly upon addition of shear stress, and gradually spread back out, with ACHN displaying a more mild response.

Next, we introduced cells into the chips. We primed each chip with 100 ug/mL fibronectin in order to coat the glass substrate with this common extracellular matrix protein, and to facilitate cell attachment. Then, we seeded the devices with Mel9, a human melanoma cell line which, in the original proposal, we listed as a candidate cell line for feasibility testing. After 4 hrs of incubation, we observed excellent cell attachment as evidenced by normal spread out morphology (FIG. 10, left column). We also observed that by adjusting seeding cell density, we could achieve ~200-300 cells per chamber, as desired.

We then exposed the cells to flow of normal cell media driven at 7.5 in $H_2O$ (0.34 psi) for 120 sec, 15 in $H_2O$ (0.68 psi) for 60 sec, or 30 in $H_2O$ (1.4 psi) for 30 sec, each sufficient to drive complete fluid exchange within the cell chamber as determined above. In each case, we observed that the majority of cells responded by balling up within 5 minutes after cessation of flow (FIG. 10, middle column). These cells were not dead because, after 90 min or more, they began to spread out again (FIG. 10, right column). We also tested ACHN cells, a human renal carcinoma cell. We found that, in response to the same flow rates, ACHN cells showed much more moderate balling response and faster recovery and re-spreading. Consequently, for the purposes of proof of feasibility, we decided to proceed forward with ACHN cells.

B.2 96-Chamber Device Flow Rates

Next, we set out to reproduce, in the 96-chamber Array-Chip device, the flow rates tolerated by the ACHN cells in the 8-chamber device. Through water/dye experiments, we determined that 30 in $H_2O$ (1.4 psi) of hydrostatic pressure could ensure complete fluid turnover within the cell chambers within 120 sec, similar to the 7.5 in $H_2O$ (0.34 psi) pressure used in the 8-chamber device (Sec. B.1). Conveniently, the 30 in $H_2O$ pressure for the 96-chamber device applied to both the fluid from the master inlet (common reagent addition mode) and fluid from the drug inlet (drug addition mode).

Finally, we used water/dye experiments to determine the minimum amount of time needed to flush out dead volumes within the device when fluid flow was driven at 30 in $H_2O$ of hydrostatic pressure. This information is needed to ensure that new fluids introduced into the device are correctly delivered to the desired location. Based on these measurements, we concluded that a simple rule of thumb for operation of the 96-chamber ArrayChip device is that every mode (e.g., cell chamber seeding, top bypass channel flush, common reagent addition, drug flush, drug addition) should be run for a minimum of 120 sec to ensure proper fluid flow.

B.3 Conclusions

We set out to determine the operating conditions needed to support cell culture within the ArrayChip device. The main parameter of interest was the flow rate tolerated by cells, since flow within microchannels can generate high amounts of mechanical shear stress. We desired to maximize the flow rate in order to minimize the time needed to ensure complete fluid turnover within the cell chamber.

Using a 8-chamber ArrayChip device, we determined the fluid exchange times at various flow rates. We observed that ACHN cells better tolerated such fluid flow than Mel9 cells, so we opted to continue testing with ACHN cells. Then, we determined the conditions needed to reproduce the flow rate in a 96-chamber device, and also determined the times needed to flush dead volumes within the device at that flow rate. Consequently, we gathered all of the data needed to begin assaying cells within the ArrayChip device, and we completed Section B.

We note that in future versions of the ArrayChip device, it is likely that more shear sensitive cell lines such as Mel9 can be accommodated by increasing the height of the cell chamber. This is because for microchannels whose width is much greater than the height, such as the cell chambers in ArrayChip, the shear stress is expected to be inversely proportional to the square of the height. Thus, small increases in chamber height can lead to large decreases in shear stress. Also, because the cell chamber contributes negligible resistance to the overall flow path due to its large width and short length, and increasing the height would even further decrease its resistance, changes in the cell chamber height should not appreciably affect the flow patterns (uniformity and flow rate) of the device.

Section C: Perform a Pilot Experiment to Screen Drugs on Cells in the Chip

We identified the optimal conditions for cell culture, as well as the flow rates needed for the drug and common reagent addition steps in Section B above. Based on these conditions, we set out to perform a pilot experiment involving cell culture, biochemical reagent (or drug) stimulation, fixation and antibody staining of the cell in a 96-chamber microfluidic chip. We then imaged the cells using a Zeiss epifluorescence microscope as well as a BD Pathway 855, a representative of the imaging equipment used in drug discovery labs in academia and industry.

C.1 Protocol for a Typical Drug Screening Cell-Based Assay in the Microfluidic Chip We adapted protocols for cell experimentation in microfluidic devices in order to enable a drug screening assay to be performed in the ArrayChip chip. A brief summary of this protocol is as follows (see FIG. 2 and FIG. 8E for modes of operation).

1) Fill the valve microchannels with distilled/deionized water pressurized at 5 psi. This pressure allows the valve microchannels to be filled up readily, without the risking separation of the chip from the glass surface.
2) Fill the chip with sterile PBS by introducing the fluid through one of the master inlets at ~20 in $H_2O$ (0.7 psi) hydrostatic pressure, while keeping the drug inlet valves closed and all other inlets and outlets plugged. Air bubbles within the device will permeate through the PDMS and be eliminated.
3) Fill the drug inlets with drug-containing solutions in one of two ways. The first method is to drive flow of PBS from the master inlet to the drug inlet, removing any PBS from the drug inlet by pipet, adding the drug solution to the drug inlet, then using drug flush mode to drive the drug solution into the chip. The second method is to pre-treat the chip to increase the hydrophilicity of the drug inlets (e.g. by oxygen plasma exposure), and adding the drug solution directly to the drug inlet. Such a treatment allows better wetting of the surface by the drug solution, and removes the need for pre-filling of the drug inlets with PBS, thus removing the chance for accidental dilution of the drug solution. After either method, apply psi air pressure to the drug inlets in order to eliminate any air bubbles in the drug inlet or corresponding channel.
4) Coat the cell chambers with 10-100 ug/mL fibronectin (or similar extracellular matrix protein) using the cell seeding mode for an hour, then wash away the fibronectin and remaining PBS with cell media.

5) Seed cells at a concentration of $9 \times 10^6$ cells/mL through one of the inlets using the cell seeding mode for 2 mins at a 30 in $H_2O$ (1.4 psi) hydrostatic pressure. Only a small portion of the cells are used during this process, and the cells can be used to seed several chips in succession. Stop fluid flow within the chip using the valves, and allow the cells to attach to the fibronectin-coated glass surface for at least 4 hours in an 37C, 5% $CO_2$ incubator.
6) Use the drug flush mode flush out dead volume in the drug inlet channels, thus bringing the drug solutions to the entrances of the cell chambers. Use drug addition mode to replace cell media within the cell chambers with the drug solutions.
7) Sequentially use the top bypass flush and cross channel flush to flush the dead volumes with fixative (e.g., 4% paraformaldehyde in PBS solution), then use the common reagent addition mode to simultaneously introduce the fixative into all of the cell chambers. Close the valves to stop all fluid flow and allow the fixation to proceed for 20 min.
8) Similarly to step 7, permeabilize the cells by introducing 0.1% triton X-100 into the cell chambers for 5 min. Likewise, apply 10% goat serum blocking solution for 1 hr, primary antibody solution for 1 hr, and secondary antibody solution for 1 hr.
9) Store the chip in the fridge with PBS attached at a small (~10 in $H_2O$ or 0.5 psi) hydrostatic pressure, with the drug inlet valve kept close and all other inlets and outlets plugged (to prevent liquid leakage).
10) Image the cell chambers using an automated microscope or imaging platform.
11) Note that all of the steps mentioned are performed in an automated manner (i.e., actuation of valves and switching between various fluid flow modes is controlled by computer).

C.2 Pilot Cell-Based Assay Experiment

Figure 11:
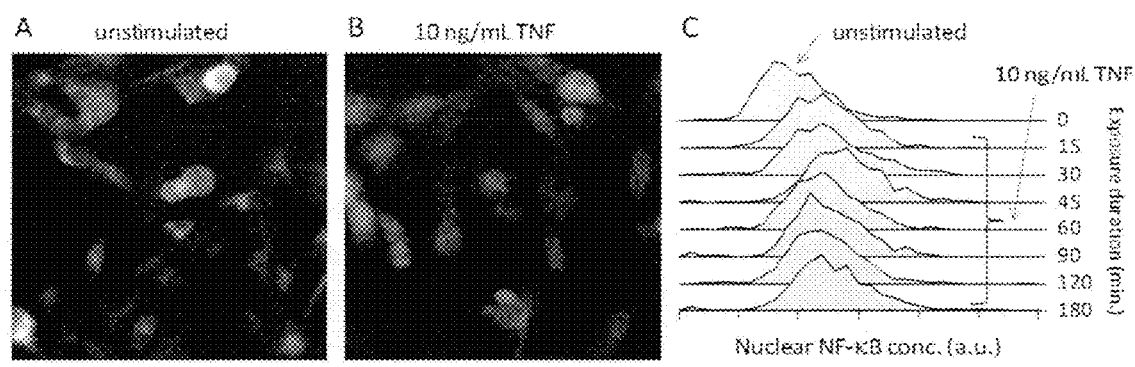
FIG. 11: Antibody staining of cells to detect nuclear translocation of NF-κB in ACHN cells in response to TNF. Validation experiment performed on glass coverslips

We performed a pilot cell-based assay experiment, involving exposure of ACHN cells to TNF, and observing nuclear translocation of the downstream transcription factor NF-κB as the readout. We verified that ACHN cells indeed sense TNF by examining their responses when cultured on glass coverslips. Using NF-κB-specific antibodies, we observed that cells that were not stimulated with TNF had NF-κB localization that was generally more cytoplasmic than nuclear, whereas cells stimulated with 10 ng/mL TNF between 15-180 min had NF-κB localization that was generally more nuclear than cytoplasmic, and there was a significant difference between the distributions of the responses between unstimulated and stimulated cells ($p<10^{-8}$) (FIG. 11).

Next, we proceeded to perform a full pilot experiment in the 96-chamber edition of ArrayChip v.2.4 according to the protocol above (Sec. C.1). We applied different concentrations of TNF to each row of the device (50, 20, 8, 3.2, 1.3, 0.5, 0.2, 0.08, 0.03, 0.01, 0.005, 0 ng/ml) representing a dose response in which each dose is applied in 8-fold replicate. We further fixed and stained the cells according to the protocol. Finally, we imaged the chip on both an automated Zeiss Axiovert 200M epifluorescence microscope (representative of equipment available to a typical academic lab) and a BD Pathway 855 imaging platform (representative of equipment available to a typical drug screening facility).

Figure 12:
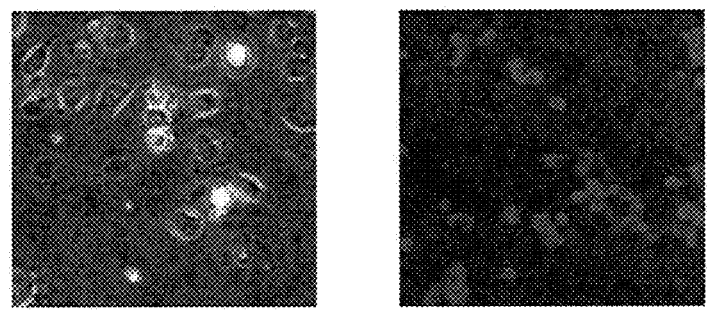
FIG. 12: Imaging of ACHN cells in a cell chamber (left). ACHN cells were fixed and stained with antibodies targeting specific signal transduction pathway proteins (right). The right panel shows a fluorescence montage of a cell chamber taken using a BD Pathway 855 imager.

Representative images of the cells are shown in FIG. 12. The images demonstrate that we were able to culture cells within the device, expose them to desired chemicals, and visualize their responses using typical cell-based assay readouts. Thus, this constitutes basic proof-of-concept that a cell-based assay can be performed in the ArrayChip chip.

C.3 Compatibility with Commercially Available Drug Screening and Research Equipment One of the unique features of the ArrayChip chip design is its grid like layout of drug inlets and cell chambers, potentially allowing for compatibility with fluid handling and imaging equipment found in drug screening divisions of pharmaceutical companies.

We determined that the ArrayChip microfluidic chip is compatible with manual pipeting methods, including multi-channel pipettors, due to the grid layout of the drug inlets. Specifically, 10 ul pipette tips, or thin gel loading-style pipette tips, enable consistent introduction of fluids to the bottom of the drug inlets. The 384-chamber version of the chip should be compatible with precise liquid handlers, because it has small sized drug inlets (~2 mm diameter). We also fully expect that the full scale 96-chamber version of the chip having 9 mm grid spacing (instead of 4.5 mm grid spacing) will be compatible with all liquid handlers, since we can incorporate bigger drug inlets in that design allowing for more tolerance for such machines.

We also tested for compatibility with commercially available microscopes. We successfully imaged the 96-chamber chip with a Zeiss Axiovert 100M inverted epifluorescence microscope without requiring any special stage inserts, since the chip is mounted on glass having a standard multi-well plate frame (see FIG. 8F). We also successfully imaged the chip on a BD Pathway 855 imager which is representative of the typical imaging equipment used in many drug screening divisions. In particular, we were able to image all 96 cell chambers of the chip in a single automated operation. Thus, we were able to display proof-of-concept of the use of this chip with key research equipment.

C.4 Conclusions

Our goal for this Section was to provide proof of concept that a cell based assay experiment can be performed inside our microfluidic chip, wherein cells are exposed to drugs or similar dissolved stimuli. We used the ACHN cell line for the experiment because of its better shear stress response, and treated these cells with a cytokine TNF.

We determined the optimal cell culture, stimulation and fixation protocol for cells inside our microfluidic chip, and performed a proof-of-concept experiment. The cells displayed viability and appropriate qualitative response during our experiment. We used manual pipetting for the chip operation, and will need to increase the size of the drug inlets in the larger 96-chamber design or use more precise liquid handlers to ensure automated liquid handling. We were also able to image the chip in a research lab setting using an epifluorescence microscope as well as a drug screening setting using a commercial BD Pathway imager.

Other Improvements and Variations

The previous section describes in detail the ArrayChip' chip design for performing cell-based drug screening assays. However, a person skilled in the art will be able to make several modifications to the chip design, operation, and applications, all of which are anticipated by this invention. Some examples of such modifications and variations include:

a) Chip design: The designs shown in previous figures (FIGS. 1,2, 6 and FIGS. 8A-8F) are only a subset of the overall set of designs that our invention anticipates. Some examples of such changes include, but are not limited to:

We have included only one test chamber and one external inlet in each reaction unit in the above figures, but alternate designs can include more than one test chamber or external inlet per reaction chamber.

We have included a top flow through channel and a bottom flow through channel in the current ArrayChip designs. An alternate design could include only of these flow-through channels or additional flow-through channels (i.e. 1, 2 or greater than 2 flow-though channels).

We have employed a resistance equalization mechanism in order to improve uniformity of flow into the cell chambers. The resistance equalization will vary depending on the specific design, and is not limited to the resistance values in FIG. 4. We have changed the resistance by changing the width and length of channels. However, one can also increase resistance by varying the height or some other flow-related property of a microfluidic channel, including the placement of deterrents or enhancers of flow within or outside the channel.

The overall height of the fluidic layer or the control/valve layer of the chips does not need to be constant. Indeed, the fluidic layer can have multiple heights e.g. the cell chambers could be made to have a higher height than the fluidic channels, which would result in reduced flow-induced shear stress on cells.

The exact placement, shape, size, grid spacing and volume of the drug inlets, cell chambers, connecting channels and valves can be varied depending on the application. In particular, the dimensions shown in FIG. 8D are only representative in nature, and can be varied by someone skilled in the art.

The ArrayChip design places the drug inlets as well as the cell chambers on a regular grid spacing based on ANSI/SBS standards for a multiwell plate. However, these elements could be placed in a non-regular grid spacing, or in an irregular fashion, depending on the application.

The ArrayChip designs in FIGS. 1 and 8 use a control layer/a valve layer that lies above the fluidic layer, and is actuated by pressure applied through liquid or gas in the control layer. However, the 'valve' is meant to be a general mechanism of regulation of fluid flow in the channels of the fluidic layer. Other mechanisms of regulation include but are not limited to electrical, magnetic, mechanical, and chemical modes of regulation.

The ArrayChip designs in FIG. 1 and FIGS. 8A-8F describe a two-layer chip/device. However, depending on the application and manufacturing process, someone skilled in the art could design a chip with 1 layer, 2 layers, 3 layers or more layers. As an example, one can design a third layer of valve control overlying the valve inlets of the current control layer, so that multiple valves in the $2^{nd}$ layer can be controlled through a single valve inlet in the $3^{rd}$ layer.

b) Chip manufacture: The ArrayChip chip designs in FIG. 1 and FIGS. 8A-8F were manufactured using soft lithography and used the polymer Polydimethylsiloxane (PDMS). In particular, a typical fabrication protocol is indicated below:

| Silicon Master Mold Fabrication - Fluidic layer. SPR 220-7 2 wafers, ArrayChip v1.0 fluidic layer | | |
|---|---|---|
| Step | Time | Notes |
| Dehydration | 200 C., 5 min | |
| HMDS coating | 1500 rpm, 10 s, ACL = 30 | |
| Evaporate | 100 C. or higher, 1 min | |
| | Let cool on benchtop for 3-5 min | |
| Coat with SPR220-7.0 | Cover almost entire wafer with resist | |
| (target height ~44-48 um) | Spin 730 rpm for 30 sec, ACL = 30 | |
| Relaxation | 10 minutes | |
| Soft bake | Start at 65 C., ramp to 115 C. (at 500 C./hour) | |
| (target height ~22 um) | Hold for 8 min (Total time is therefore 15 minutes) | |
| | Ramp back to room temp | |
| Rehydration | Let sit ~1 hr at room temperature | 22-23 um by Filmetrics |
| Expose | 630 mJ/cm² without 360 nm filter | Elapsed exposure time ~68 sec |
| Develop | ~5 min in 100% MF-26A | |
| Gently rinse with running DI water. | | |
| Post-development rounding bake. | Ramp to 125 C. at 540 C./hour. Hold for 15 minutes. (Total baking time is therefore 25 minutes.) Ramp back to room temp | 30.8 um peak height by profilometry |

| Silicon Master Mold Fabrication - control layer, SU8-2025 2 wafers, ArrayChip v1.0 control layer 101.45% mag | | |
|---|---|---|
| Step | Time | Check |
| Dehydration | 200 C., 5 min | |
| Coat with SU8-2025 | For 3" wafer, cover ½ area | |
| (Target height ~35-45 um) | Spin 1700 rpm, 70 s, ACL = 2 (208 rpm/s) | |
| Soft bake | Start at 65 C., ramp to 95 C. | |
| Cover the wafer with glass dish. | Set time for 2:05 hours | |
| Leave gap for solvent evaporation. | Ramp back to room temp | |

| Step | Time | Check |
|---|---|---|
| | Silicon Master Mold Fabrication - control layer, SU8-2025 2 wafers, ArrayChip v1.0 control layer 101.45% mag | |
| Expose | 2000 mJ/cm$^2$ with 360 nm filter | Elapsed exposure 3 min 38 sec |
| Post exposure bake | Ramp to 95 C., hold for 1 hour Ramp back to room temp | |
| Develop | Dropper on SU8 developer | |
| Rinse | Dropper rinse in IPA Let dry in ambient air (do not use airgun) | |
| Adherence bake | Ramp to 200 C., total time 30 min Ramp to room temp | 30.0 um height by profilometry |

It must be noted that those skilled in the art will be able to modify several steps and/or parameters of the fabrication process in order to achieve the same or similar result. Our invention anticipates such improvements or modifications to the chip manufacturing process. In particular:

The chip manufacture can be done using soft lithography, injection molding, hot embossing or several other microfluidic manufacturing techniques known to those skilled in the art.

The chip material does not have to be limited to PDMS, and can include other polymers, elastomers, plastics, glass, silicon or other microfluidic chip manufacturing materials.

c) Chip applications: The ArrayChip chip application in this document was described for cell-based assays for drug screening. However, this chip design or variations of it, can be used for a variety of biological, non-biological, chemical, molecular biology, biochemistry, enzymatic or cell-based assay applications. As an example, these applications include but are not limited to:

This document discusses the usage of melanoma and ACHN cell lines. However, the chip can be used for all kinds of cell types, including but not limited to yeast, bacteria, viruses, mammalian cell lines, primary cells obtained from humans or animals, tissue biopsy cells, blood-derived cells, stem cells (e.g. embryonic stem cells, induced pluripotent stem cells), stem cell-derived cells etc.

The chip can be used for applications including but not limited to, drug exposure to cells as part of drug screening, drug discovery, diagnostic applications etc. This also includes assays involving small biochemical molecules, biologics such as antibodies, RNA interference assays, etc. The end points of these assays could be visual phenotypic observation, as well as detection mechanisms involving fluorescence or light-based readouts, thermal readouts, electrical readouts, chemical readouts etc.

The chip can be used for molecular biology, biochemistry or enzymatic assay applications e.g.

PCR, RT-PCR, qPCR, qRT-PCR, gene sequencing, genome sequencing, sanger sequencing, next generation sequencing, ELISA etc.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A microfluidic device for performance of chemical, biochemical or cellular assays, comprising an array of reaction units:
   wherein, each reaction unit comprises a test chamber where a chemical, biochemical or cellular assay is performed,
   wherein, each reaction unit further comprises of an external inlet that is specific to that reaction unit and is operably connected to the test chamber,
   wherein, each reaction unit further comprises a central channel that is operably connected to the test chamber,
   wherein, each reaction unit further comprises at least one top fluidic channel, or at least one bottom fluidic channel, or at least one top and bottom fluidic channel, that are each operably connected to the test chamber, wherein fluid can flow through a top or bottom channel without passing through the test chamber,
   wherein, each reaction unit contains control elements that can dynamically control the flow of fluid and particles between the test chamber and the external inlet, the test chamber and the central channel, the test chamber and the top channel, the test chamber and the bottom channel, and/or between the reaction unit and an adjoining reaction unit,
   wherein, a set of reaction units is operably connected to at least one inlet and at least one outlet corresponding to that set of reaction units, which are distinct from the external inlets specific to each reaction unit,
   wherein, a set of reaction units contains control elements that can dynamically control the flow of fluid and particles between reaction units within the set,
   wherein, the microfluidic device contains control elements that can control the flow of fluid and particles between the different reaction units.

2. The microfluidic device of claim 1, wherein the array of reaction units are arranged in a grid wherein the distance between adjoining reaction units along the horizontal (row) and vertical (column) directions (pitch size) is the same, and stays constant throughout the grid.

3. The microfluidic device of claim 1, wherein the array of reaction units are arranged in a grid wherein the distance between adjoining reaction units in the horizontal (row) and vertical (column) direction is different and can vary across the grid.

4. The microfluidic device of claim 1, wherein each reaction unit contains one test chamber and at least two external inlets, or each reaction unit contains at least 2 test chambers and one external inlet, or each reaction unit contains at least two test chambers and at least two external inlets.

5. The microfluidic device of claim 2, wherein the total number of reaction units in the microfluidic device is 96, said reaction units are arranged in an 8×12 grid with a constant pitch, the pitch size of the reaction units is approximately 9 mm, and the size of each reaction unit is approximately 9 mm×9 mm, and an outside footprint of approximately 127.76 mm×85.48 mm.

6. The microfluidic device of claim 2, wherein the center of the external inlet of each reaction unit coincides with the center of a well of an multiwell plate, and the size and dimensions of the entire reaction unit are contained within the size and dimensions of the well of a multiwell plate.

7. The microfluidic device of claim 2, wherein the overall dimensions of the microfluidic device, the total number of reaction units, the arrangement of reaction units into rows and columns, the location of reaction units, the pitch size of reaction units, and the size and dimensions of each reaction unit, are the for multiwell plates, and the total number of reaction units are selected from the group consisting of six wells, 12 wells, 24 wells, 48 well, 96 wells, 384 wells, 1536 wells, and 3456 wells.

8. The microfluidic device of claim 1, wherein the control elements consist of valves that are actuated by liquid pressure, gas pressure, mechanical pressure, electronically or magnetically.

9. The microfluidic device of claim 8, wherein the control elements are present in a control layer that is placed either above or below the fluidic layer containing the reaction units.

10. The microfluidic device of claim 8, wherein the control elements are present in two different layers, the control layer and the supercontrol layer, that are distinct from the fluidic layer containing the reaction units, and the control layer is placed either directly above or below the fluidic layer, and the supercontrol layer is placed either directly above or below the control layer, wherein the control layer is between the supercontrol layer and the fluidic layer.

11. The microfluidic device of claim 9, wherein at least one control channel is connected to valves in more than one reaction unit, wherein the valves have the same relative position and function within each reaction unit, and the valves are sequentially actuated by the control channel.

12. The microfluidic device of claim 10, wherein at least one control channel is connected to valves in more than one reaction unit, wherein the valves have the same relative position and function within each reaction unit, and wherein more than one control channel is further connected to and actuated by at least one supercontrol channel in the supercontrol layer.

13. The microfluidic device of claim 8, wherein the actuation of different sets of valves leads to different flow patterns of fluids and particles, wherein operation of said microfluidic device includes at least one flow pattern that leads to cell seeding in the test chambers, flushing of drugs or other chemicals through the bottom channel without passing through the test chamber, test chamber isolation, drug addition to the chamber from the external inlet, common reagents flushing through the top and bottom channels, and/or addition of common reagents through the test chamber.

14. The microfluidic device of claim 1, wherein for each reaction unit, at least one of the following, the dimensions and structure of the channel connecting the top channel to the test chamber, the dimensions and structure of the channel connecting the bottom channel to the test chamber, and/or the dimensions and structure of the channel connecting the external inlet to the test chamber, are modified so as to change their fluidic resistance and to ensure an essentially equal flow rate and an essentially equal time of introduction of fluid and particles to the test chamber.

15. The microfluidic device of claim 14, wherein the dimensions and structure of the channels can be varied by changing the height, width, length, cross-sectional shape, and/or topological shape, of the fluidic channel, or a combination of the height, width, length, cross-sectional shape, and/or topological shape, of the fluidic channel, and/or by adding physical deterrents or enhancers of flow in the channel path.

16. The microfluidic device of claim 1, wherein the device is composed of a biocompatible, optically clear, gas permeable elastomer.

17. The microfluidic device of claim 1, wherein the device is composed of a polymeric material selected from the group consisting of polydimethylsulfoxide, polyisoprene, polybutadiene, polychloroprene, polyisobutylene, poly(styrene-butadiene-styrene), the polyurethanes, and silicone polymers; or poly(bis(fluoroalkoxy)phosphazene), poly(carborane-siloxanes), poly(acrylonitrile-butadiene), poly(1-butene), poly(chlorotrifluoroethylene-vinylidene fluoride) copolymers, poly(ethyl vinyl ether), poly(vinylidene fluoride), poly(vinylidene fluoride-hexafluoropropylene) copolymer, elastomeric compositions of polyvinylchloride, polysulfone, polycarbonate, polymethylmethacrylate, or polytertrafluoroethylene.

18. The microfluidic device of claim 1, wherein the external inlet size is designed to allow the introduction of chemicals, biochemicals, growth media, particles or cells, drugs, growth factors, cytokines, inhibitors, effectors, antigens, antibodies, dyes, living cells, dead cells, or primary cells, buffers, fixation media, or washing media, wherein the fluid introduction is done using a pipette tip attached to a manual or automated pipettor, or a fluidic connector, and flow through the external inlet is driven by gravity or external pressure or vacuum.

19. The microfluidic device of claim 1, wherein the network of fluid channels connecting an inlet and outlet to its corresponding set of reaction units consists of a branching network where a single channel branches out into multiple channels from a common junction, leading to an essentially equal distribution of particles, cells, chemicals or biochemicals.

20. The microfluidic device of claim 1, wherein the central channel that is operably connected to the test chamber is composed of smaller central channels, wherein fluid flow through the central channel is selected from one of two modes, fluid flow passes through the test chamber via a set of smaller central channels, or fluid flow passes through a different set of smaller central channels flanking the test chamber without passing through the test chamber.

* * * * *